(12) United States Patent
Patil et al.

(10) Patent No.: US 10,323,204 B2
(45) Date of Patent: *Jun. 18, 2019

(54) LOW VISCOSITY, LOW VOLATILITY LUBRICATING OIL BASESTOCKS

(71) Applicant: ExxonMobil Research and Engineering Company, Annandale, NJ (US)

(72) Inventors: Abhimanyu O. Patil, Westfield, NJ (US); Satish Bodige, Wayne, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 326 days.

This patent is subject to a terminal disclaimer.

(21) Appl. No.: 14/496,268

(22) Filed: Sep. 25, 2014

(65) Prior Publication Data

US 2015/0119307 A1    Apr. 30, 2015

Related U.S. Application Data

(60) Provisional application No. 61/895,436, filed on Oct. 25, 2013.

(51) Int. Cl.
| | |
|---|---|
| *C10M 107/34* | (2006.01) |
| *C10M 105/18* | (2006.01) |
| *C07C 41/01* | (2006.01) |
| *C07C 43/263* | (2006.01) |
| *C07C 43/205* | (2006.01) |
| *C07C 41/16* | (2006.01) |

(52) U.S. Cl.
CPC .......... *C10M 105/18* (2013.01); *C07C 41/01* (2013.01); *C07C 41/16* (2013.01); *C07C 43/2055* (2013.01); *C07C 43/263* (2013.01); *C10M 2203/1006* (2013.01); *C10M 2203/1025* (2013.01); *C10M 2205/0285* (2013.01); *C10M 2207/0406* (2013.01); *C10N 2220/022* (2013.01); *C10N 2230/70* (2013.01); *C10N 2230/74* (2013.01); *C10N 2270/00* (2013.01)

(58) Field of Classification Search
CPC .......... C10M 105/18; C10M 2209/103; C10M 129/16
USPC ......................................... 508/580
See application file for complete search history.

(56) References Cited

U.S. PATENT DOCUMENTS

| | | |
|---|---|---|
| 2,067,960 A | 1/1937 | Werntz |
| 2,665,253 A | 1/1954 | Hollibaugh |
| 3,036,003 A | 5/1962 | Verdol |
| 3,172,892 A | 3/1965 | Le Suer et al. |
| 3,219,666 A | 11/1965 | Norman et al. |
| 3,316,177 A | 4/1967 | Dorer, Jr. |
| 4,234,435 A | 11/1980 | Meinhardt et al. |
| 4,642,349 A | 2/1987 | Renga |
| 4,827,064 A | 5/1989 | Wu |
| 4,827,073 A | 5/1989 | Wu |
| 4,889,647 A | 12/1989 | Rowan et al. |

(Continued)

FOREIGN PATENT DOCUMENTS

| | | |
|---|---|---|
| CN | 1504446 A | 6/2004 |
| EP | 1201734 A1 | 2/2002 |

(Continued)

OTHER PUBLICATIONS

The International Search Report and Written opinion of PCT/US2014/057394 dated Dec. 16, 2014.

(Continued)

*Primary Examiner* — Prem C Singh
*Assistant Examiner* — Francis C Campanell
(74) *Attorney, Agent, or Firm* — Robert A. Migliorini; Kristina Okafor

(57) ABSTRACT

This disclosure provides low viscosity, low volatility aryl ether compounds represented by formula (1):

(1)

and represented by formula (2):

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8. This disclosure also provides processes for producing the aryl ether compounds, lubricating oil basestocks and lubricating oils containing one or more of the aryl ether compounds, and a method for improving one or more of solubility and dispersancy of polar additives and/or sludge in a lubricating oil by using as the lubricating oil a formulated oil containing one or more of the aryl ether compounds.

17 Claims, 3 Drawing Sheets

(56) References Cited

U.S. PATENT DOCUMENTS

| | | | |
|---|---|---|---|
| 4,956,122 A | | 9/1990 | Watts et al. |
| 4,978,464 A | | 12/1990 | Coyle et al. |
| 5,639,719 A | * | 6/1997 | Tanaka .................. C10M 105/18 |
| | | | 252/68 |
| 5,705,458 A | | 1/1998 | Roby et al. |
| 6,406,642 B1 | * | 6/2002 | Enna ....................... C09K 5/045 |
| | | | 252/67 |
| 2006/0166844 A1 | * | 7/2006 | Egawa ................. C10M 105/18 |
| | | | 508/579 |

FOREIGN PATENT DOCUMENTS

| | | |
|---|---|---|
| EP | 1040115 B1 | 6/2004 |
| JP | 59015489 A | 1/1984 |
| JP | 06128583 A | 5/1994 |
| JP | 06220723 A | 8/1994 |
| JP | 10245582 A | 9/1998 |
| WO | 99/31113 A1 | 6/1999 |

OTHER PUBLICATIONS

Yelamaggad, Channabasaveshwar V. et al., "A New Class of Discotic Mesogens Derived from Tris (N-salicylideneaniline)s Existing in C3/t and Cs Keto-Enamine Forms," The Journal of Organic Chemistry, 2007, vol. 72, pp. 8308-8318.

Chapuzet, Jean-Marc et al., "A Versatile Anodic Source of Triphenylenes Possessing at Least One Ionophoric Site," Tetrahedron Letters, 1991, vol. 32, Issue 50, pp. 7405-7408, Great Britain.

Lee, Eun et al., "Radical Isomerization via Intramolecular Ipso Substitution of Aryl Ethers: Aryl Translocation from Oxygen to Carbon," Tetrahedron Letters, 1993, vol. 34, Issue 14, pp. 2343-2346, Great Britain.

Ishizaki, Miyuki et al., "Palladium charcoal-catalyzed deprotection of O-allylphenols," Tetrahedron 60, 2004, pp. 7973-7981.

Pak, Joshua et al., "An efficient synthesis of 4,4',5,5'-tetraiododibenzo-24-crown-8 and its highly conjugated derivatives," Tetrahedron Letters 47, 2006, pp. 233-237.

Naidu, Ajay et al., "An efficient intermolecular BINAM-copper(I) catalyzed Ullmann-type coupling of aryl iodides/bromides with aliphatic alcohols," Tetrahedron Letters 49, 2008, pp. 3147-3151.

Zhou, Hongjun et al., "Highly Selective Fluorescent Recognition of Sulfate in Water by Two Rigid Tetrakisimidazolium Macrocycles with Peripheral Chains," Journal of the American Chemical Society, 2013, vol. 135, Issue 40, pp. 14908-14911.

Wolter, Martina et al., "Copper-Catalyzed Coupling of Aryl Iodides with Aliphatic Alcohols," Organic Letters, 2002, vol. 4, No. 6, pp. 973-976.

Brown, B.B. et al., "Preparation, Refractive Indices, and Boiling Points of Certain Organic Liquids," Journal of Chemical and Engineering Data, 1961, vol. 6, pp. 52-56.

Mehta, T. N. et al., "Halogenation of fatty acids. III. Reaction between alkyl halides with phenols. Formation of long-chain alkyl ethers" (Abstract Only), Journal of the Indian Chemical Society, Industrial and News Edition, 1941, vol. 4, pp. 170-174.

* cited by examiner

LOW VISCOSITY, LOW VOLATILITY LUBRICATING OIL BASESTOCKS

CROSS-REFERENCE TO RELATED APPLICATIONS

This application claims priority to U.S. Provisional Application Ser. No. 61/895,436 filed Oct. 25, 2013, which is herein incorporated by reference in its entirety.

FIELD

This disclosure relates to low viscosity, low volatility aryl ether compounds, processes for producing the aryl ether compounds, lubricating oil basestocks and lubricating oils containing one or more of the aryl ether compounds, and a method for improving one or more of solubility and dispersancy of polar additives and/or sludge in a lubricating oil by using as the lubricating oil a formulated oil containing one or more of the aryl ether compounds.

BACKGROUND

Lubricants in commercial use today are prepared from a variety of natural and synthetic basestocks admixed with various additive packages and solvents depending upon their intended application. The basestocks typically include mineral oils, polyalphaolefins (PAO), gas-to-liquid base oils (GTL), silicone oils, phosphate esters, diesters, polyol esters, and the like.

A major trend for passenger car engine oils (PCEOs) is an overall improvement in quality as higher quality basestocks become more readily available. Typically the highest quality PCEO products are formulated with basestocks such as PAOs or GTL stocks.

PAOs and GTL stocks are an important class of lube basestocks with many excellent lubricating properties, including high viscosity index (VI) but have low polarity. This low polarity leads to low solubility and dispersancy for polar additives and/or sludge generated during service. These basestocks require the use of cobasestocks to improve additive and deposit solubility.

Therefore, there is a need for polar cobase fluids that provide appropriate solubility and dispersibility for polar additives and/or sludge generated during service of lubricating oils.

The present disclosure also provides many additional advantages, which shall become apparent as described below.

SUMMARY OF THE DISCLOSURE

This disclosure provides oxygen-containing polar and hydrolytically stable Group V basestocks. Unlike Group V esters, the fluids of this disclosure are hydrolytically stable, and unlike alkylated naphthalene (AN) Group V basestocks, the fluids of this disclosure contain oxygen functionality and are more polar. The aryl ether containing fluids of this disclosure have surprisingly good lubricant properties. Moreover, the aryl ether containing fluids of this disclosure have surprisingly lower friction coefficient than PAOs of similar viscosity, thus providing fuel economy advantages. The aryl ether-containing fluids of this disclosure are organic molecules containing hydrocarbon and ether segments with precise structure (i.e., not oligomers or polymers).

This disclosure relates in part to a compound represented by formula (1):

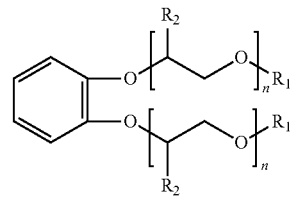

or a compound represented by formula (2):

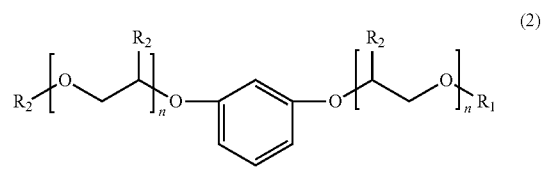

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

This disclosure also relates in part to a mixture comprising: two or more compounds represented by formula (1); two or more compounds represented by formula (2); or two or more compounds represented by formula (1) and formula (2).

This disclosure further relates in part to a process for producing a compound represented by formula (1):

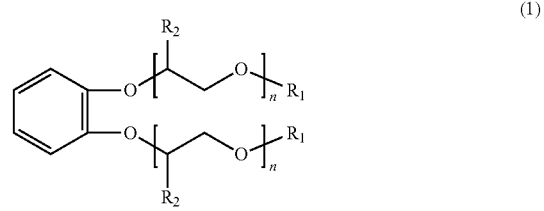

or a compound represented by formula (2):

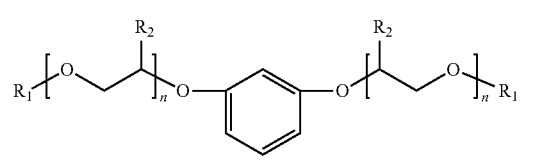

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8. The process comprises reacting an aryl halide with an alcohol, in the presence of a catalyst, under reaction conditions sufficient to produce the compound represented by formula (1) or the compound represented by formula (2).

This disclosure yet further relates in part to a process for producing a compound represented by formula (1):

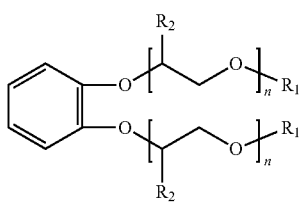

(1)

or a compound represented by formula (2):

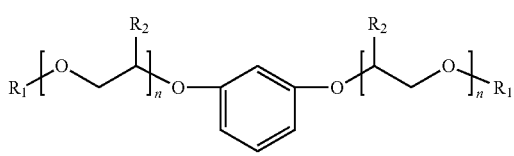

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8. The process comprises reacting an aryl diol with an alkyl halide, in the presence of a catalyst, under reaction conditions sufficient to produce the compound represented by formula (1) or the compound represented by formula (2).

This disclosure also relates in part to a lubricating oil basestock comprising one or more compounds represented by formula (1):

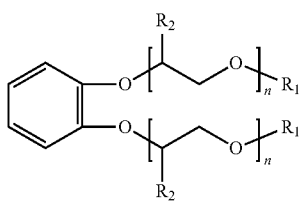

(1)

and/or by formula (2):

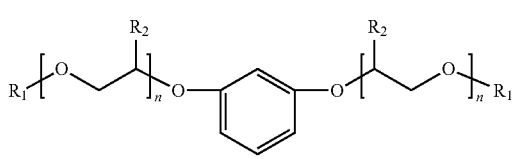

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

This disclosure further relates in part to a lubricating oil comprising a lubricating oil basestock as a major component, and a lubricating oil cobasestock as a minor component. The lubricating oil cobasestock is represented by formula (1):

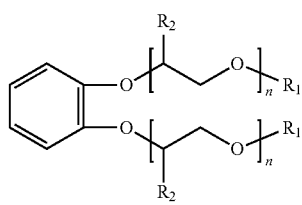

(1)

or by formula (2):

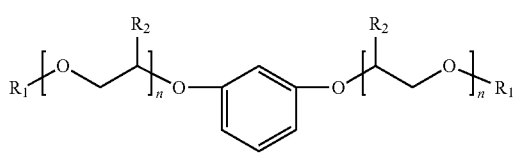

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

This disclosure yet further relates in part to a method for improving one or more of solubility and dispersancy of polar additives or sludge in a lubricating oil by using as the lubricating oil a formulated oil comprising a lubricating oil basestock as a major component, and a lubricating oil cobasestock as a minor component. The lubricating oil cobasestock comprises one or more compounds represented by formula (1):

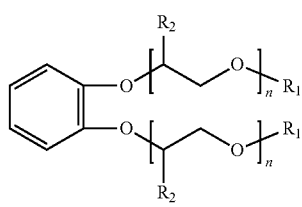

(1)

or one or more compounds represented by formula (2):

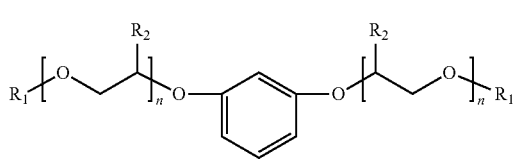

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

In addition to improved solubility and dispersibility for polar additives and/or sludge generated during service of lubricating oils, improved fuel efficiency can also be attained in an engine lubricated with a lubricating oil by using as the lubricating oil a formulated oil in accordance with this disclosure. The formulated oil comprises a lubricating oil basestock as a major component, and an aryl ether-containing, lubricating oil cobasestock as a minor component. The lubricating oils of this disclosure are particularly advantageous as passenger vehicle engine oil (PVEO) products. Optionally, the formulated oil comprises a lubricating oil basestock as a minor component, and an aryl ether-containing, lubricating oil cobasestock as a major component.

Further objects, features and advantages of the present disclosure will be understood by reference to the following drawings and detailed description.

DETAILED DESCRIPTION

Figure 1:
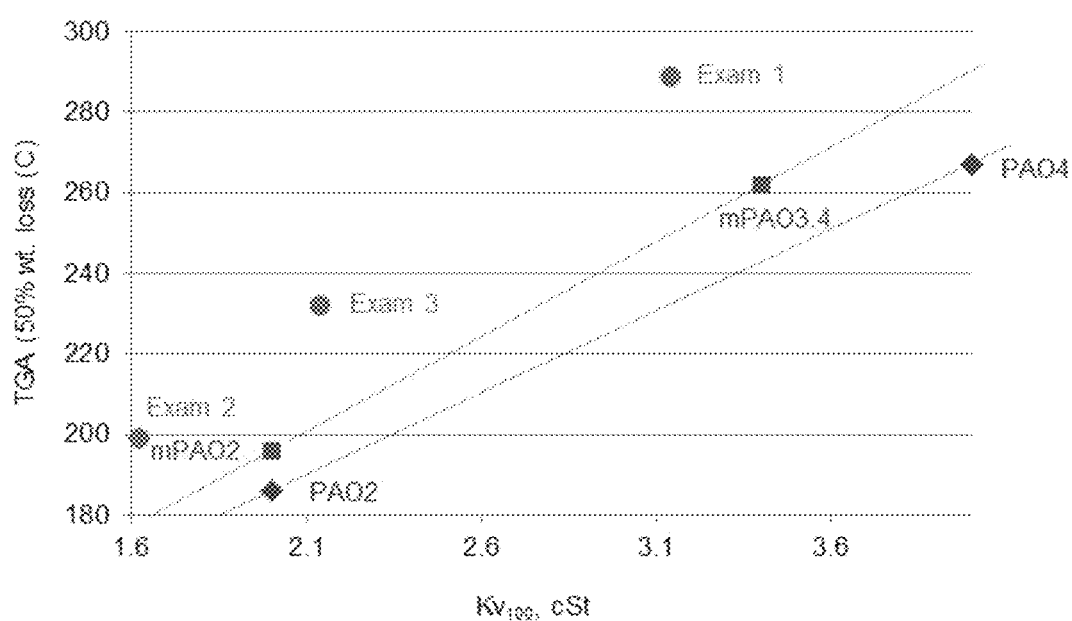
FIG. 1 graphically depicts thermogravimetric analysis (TGA) (50% wt. loss) of the aryl ether fluids of Examples 1-3 and PAOs of various viscosities.

All numerical values within the detailed description and the claims herein are modified by "about" or "approximately" the indicated value, and take into account experimental error and variations that would be expected by a person having ordinary skill in the art.

In an embodiment, this disclosure relates to aryl ether-containing Low Viscosity Low Volatility (LVLV) synthetic basestocks. The products exhibit good lubricant properties.

The aryl ether compounds of this disclosure possess low viscosity, low Noack volatility and superior low temperature properties. The aryl ether compounds of this disclosure exhibit excellent bulk flow properties with built-in polarity. The aryl ether-containing fluids of this disclosure are organic molecules containing hydrocarbon and ether segments with precise structure (i.e., not oligomers or polymers).

As indicated above, the fluids of this disclosure comprise one or more compounds represented by formula (1):

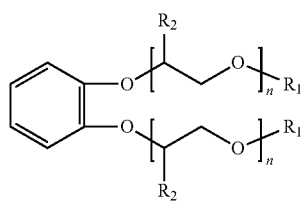
(1)

or one or more compounds represented by formula (2):

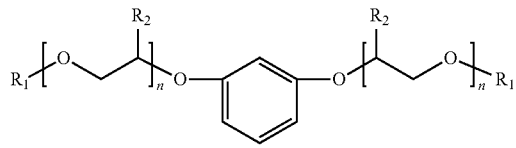
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

The compounds of this disclosure include mixtures. Illustrative mixtures include, for example, two or more compounds represented by formula (1); two or more compounds represented by formula (2); and two or more compounds represented by formula (1) and formula (2).

The compounds of this disclosure have a viscosity (Kv100) from 1 to 30 cSt at 100° C., preferably from 1.25 to 10 cSt at 100° C., and more preferably from 1.5 to 5 cSt at 100° C. The composition has a viscosity (Kv40) from 1 to 50 cSt at 40° C., preferably from 2 to 40 cSt at 40° C., and more preferably from 2.5 to 25 cSt at 40° C. The composition has a viscosity index (VI) from 20 to 200, preferably from 25 to 175, and more preferably from 30 to 150. As used herein, viscosity (Kv100) is determined by ASTM D 445-01, viscosity (Kv40) is determined by ASTM D 445-01, and viscosity index (VI) is determined by ASTM D 2270-93 (1998).

The compounds of this disclosure have a Noack volatility of no greater than 50 percent, preferably no greater than 40 percent, and more preferably no greater than 30 percent. As used herein, Noack volatility is determined by ASTM D-5800. In particular, the compounds of this disclosure can function in engines without volatilization at specific temperatures (e.g., 247-249° C., Noack conditions).

Illustrative $R_1$ substituents include, for example, linear or branched alkyl groups having from 1 to 20 carbon atoms, preferably linear or branched alkyl groups having from 1 to 10 carbon atoms, and more preferably linear or branched alkyl groups having from 1 to 8 carbon atoms. Illustrative $R_1$ substituents include, for example, methyl, ethyl, propyl, butyl, pentyl, hexyl, heptyl, octyl, and the like. Illustrative $R_2$ substituents include, for example, hydrogen and alkyl groups having from 1 to 4 carbon atoms (e.g., methyl, ethyl, propyl, butyl, and the like). Values of n can range from 0 to 8, preferably from 0 to 6, and more preferably from 0 to 4.

This disclosure also relates in part to a compound represented by formula (3):

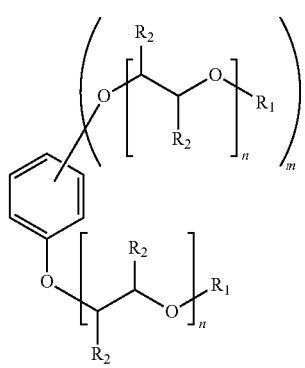
(3)

wherein $R_1$ is the same or different and is a linear or branched alkyl group having from 1 to 20 carbon atoms; $R_2$ is the same or different and is hydrogen or an alkyl group having from 1 to 4 carbon atoms; n is the same or different and is a value from 0 to 8; and m is a value from 0 to 5.

This disclosure further relates in part to a compound represented by formula (4):

(4)

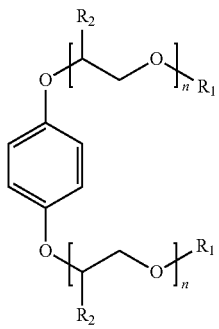

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

This disclosure yet further relates in part to a compound represented by formula (5):

(5)

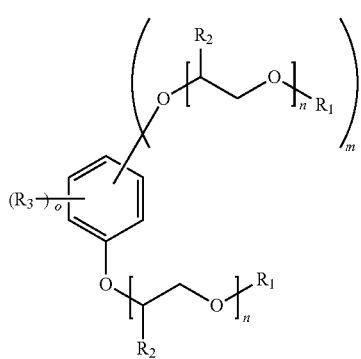

wherein $R_1$ is the same or different and is a linear or branched alkyl group having from 1 to 20 carbon atoms; $R_2$ is the same or different and is hydrogen or an alkyl group having from 1 to 4 carbon atoms; $R_3$ is the same or different and is hydrogen or a linear or branched alkyl group having from 1 to 20 carbon atoms or any other heteroatom such as F, Cl, Br; o is a value from 0 to 5 provided o+m is equal to 5; n is the same or different and is a value from 0 to 8; and m is a value from 0 to 5.

This disclosure also relates in part to a compound represented by formula (6):

(6)

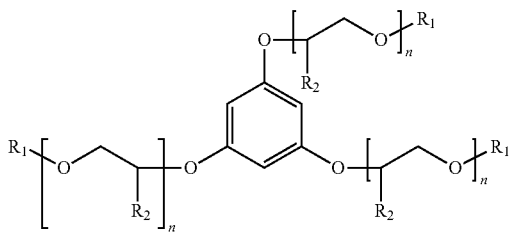

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

The embodiments of this disclosure as described herein with respect to the compounds of formulae (1) and (2) apply equally to the compounds of formulae (3), (4), (5) and (6).

Illustrative compounds of formula (1) include, for example those represented by the formula:

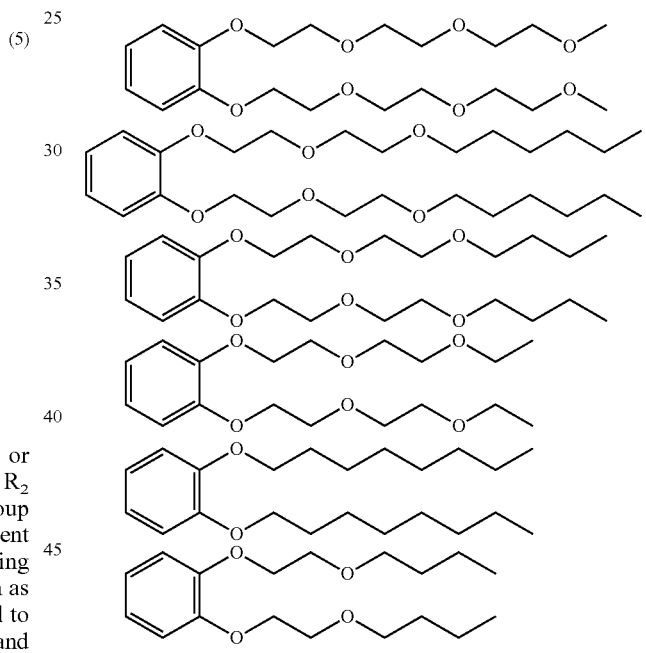

Illustrative compounds of formula (2) include, for example those represented by the formula:

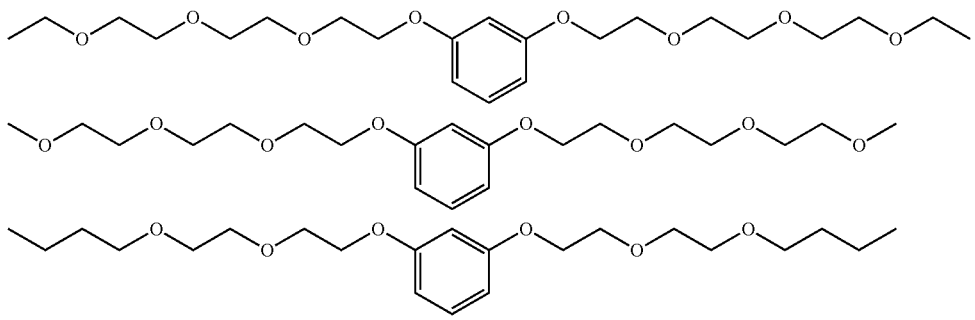

Illustrative compounds of this disclosure include, for example, aryl ethers. Preferred aryl ether compounds result from the reaction of an aryl halide with an alcohol, under reaction conditions sufficient to produce a compound represented by formula (1) or a compound represented by formula (2). Other preferred aryl ether compounds result from the reaction of an aryl diol with an alkyl halide, under reaction conditions sufficient to produce a compound represented by formula (1) or a compound represented by formula (2).

The compounds of this disclosure can be prepared by a process that involves reacting an aryl halide with an alcohol. The reaction is carried out in the presence of a catalyst. The reaction is also carried out under reaction conditions sufficient to produce a compound represented by formula (1) and/or a compound represented by formula (2).

Illustrative aryl halides useful in the process of this disclosure include, for example, benzyl halides such as 1,2-diiodobenzene, 1-iodobenzene, 1,3-diiodobenzene, and the like.

Illustrative alcohols useful in the process of this disclosure include, for example, primary or secondary, branched or unbranched, even or odd numbered alcohol, having from 6 to 20 carbon atoms. Preferred alcohols include, for example, Oxo alcohols and glycol ethers.

Preferred alcohols useful in the process of this disclosure include, for example, $C_8$-$C_{13}$ Oxo alcohols, glycol ethers, and the like. The alcohols can be primary or secondary, linear or branched alcohols with alkyl carbon chain length of $C_4$-$C_{20}$ carbons. Higher alcohols in the range $C_6$-$C_{18}$ are of particular industrial significance. This disclosure encompasses the whole group of primary and secondary, branched and unbranched, even- and odd-numbered alcohols.

Illustrative aliphatic alcohols useful in the process of this disclosure include, for example, methanol, ethanol, 1-propanol, 2-propanol, 1-butanol, (n-butanol), tert-butanol, 1-pentanols, 1-hexanol, 1-heptanols, 1-octanol, 1-nonanol, 1-decanol, 1-dodecanol, 1-hexadecanol, 1-octadecanol, cyclohexanol, 2,4,4-trimethyl-2-pentanol, and the like, or combination of those.

Illustrative alkyl alcohols useful in the process of this disclosure include, for example, decyl alcohol, and the like. The alkyl alcohols can be primary or secondary, linear or branched alcohols with alkyl carbon chain length of $C_4$-$C_{20}$ carbons. Higher monohydric alcohols in the range $C_6$-$C_{18}$ are of particular industrial significance. This disclosure encompasses the whole group of primary and secondary, branched and unbranched, even- and odd-numbered alcohols.

The $C_6$-$C_{11}$ and $C_{12}$-$C_{18}$ alcohols are used as 'plasticizer alcohols' and 'detergent alcohols'. Other alcohols are fatty alcohols that are available as natural products. Fats and oils from renewable resources such as rapeseed, sunflower seed, and flaxseed have been used increasingly as raw materials for alcohol production.

'Oxo' alcohols are high volume inexpensive materials and can be useful in the process of this disclosure. 'Oxo' alcohols with chain length of $C_4$-$C_6$ are mainly used, directly or after esterification with carboxylic acid (e.g., acetic acid), as solvents for the paint and plastic industry. The $C_8$-$C_{13}$ 'Oxo' alcohols obtained from olefin oligomers (e.g., isoheptenes, diisobutenes, tripropenes) on reaction with phthalic anhydride are used as PVC plasticizers.

Other types of alcohols useful in the process of this disclosure include glycol ethers. For example, one can be use glycol ethers like di(ethylene glycol) monohexyl ether, tri(ethylene glycol) monomethyl ether, tri(propylene glycol) monomethyl ether, tri(ethylene glycol) monoethyl ether, tri(ethylene glycol) monobutyl ether, di(ethylene glycol) monoethyl ether, di(ethylene glycol) monobutyl ether, tri (propylene glycol) monopropyl ether, tri(propylene glycol) monobutyl ether, poly (ethylene glycol) dodecyl ether (Brij 30), ethylene glycol mono-2-ethylhexyl ether, diethylene glycol hexadecylether, and the like.

Illustrative glycol ethers include, for example, glycol ethers with both an ether and alcohol functional group in the same molecule. The Dow Chemical Company manufactures these glycol ether molecules in large quantities. DOW® glycol ether products are produced through continuous processes of selectively reacting an alcohol (ethanol, butanol, hexanol) with ethylene oxide. Diethylene glycol monohexyl ether [($C_6H_{13}$(O$CH_2CH_2$)$_2$OH, Hexyl CARBITOL® Solvent) displays a strong hydrocarbon-type solvency.

Illustrative catalysts that can be used in the process of this disclosure include, for example, metal halide catalysts such as copper (I) iodide, and the like. The catalyst can be used in conventional amounts needed to catalyze the reaction of the aryl halide and the alcohol.

Other illustrative reaction ingredients include, for example, solvents such as toluene, xylene, decane, hexane, heptanes, and the like.

Reaction conditions for the reaction of the aryl halide with the alcohol, such as temperature, pressure and contact time, may also vary greatly and any suitable combination of such conditions may be employed herein. The reaction temperature may range between 25° C. to 250° C., and preferably between 30° C. to 200° C., and more preferably between 60° C. to 150° C. Normally the reaction is carried out under ambient pressure and the contact time may vary from a matter of seconds or minutes to a few hours or greater. The reactants can be added to the reaction mixture or combined in any order. The stir time employed can range from 0.5 to 48 hours, preferably from 1 to 36 hours, and more preferably from 2 to 24 hours.

Alternatively, the compounds of this disclosure can be prepared by a process that involves reacting an aryl diol with an alkyl halide. The reaction is carried out in the presence of a catalyst. The reaction is also carried out under reaction conditions sufficient to produce a compound represented by formula (1) and/or a compound represented by formula (2).

Illustrative aryl diols useful in the process of this disclosure include, for example, benzyl diols such as catechol, resorcinol, hydroquinone, naphthohydroquinone, and the like.

Illustrative alkyl halides useful in the process of this disclosure include, for example, 1-bromooctane, 1-iodooctane, and the like.

Illustrative catalysts that can be used in the aryl diol-alkyl halide reaction of this disclosure include, for example, $K_2CO_3$, $Cs_2CO_3$, $Na_2CO_3$, NaOH, CaOH, $K_3PO_4$, and the like. The catalyst can be used in conventional amounts needed to catalyze the reaction of the aryl diol and the alkyl halide.

Other illustrative reaction ingredients include, for example, solvents such as acetone, acetonitrile, methylene chloride, water, and the like.

Reaction conditions for the reaction of the aryl diol with the alkyl halide, such as temperature, pressure and contact time, may also vary greatly and any suitable combination of such conditions may be employed herein. The reaction temperature may range between 25° C. to 250° C., and preferably between 30° C. to 200° C., and more preferably between 60° C. to 150° C. Normally the reaction is carried out under ambient pressure and the contact time may vary from a matter of seconds or minutes to a few hours or greater. The reactants can be added to the reaction mixture or combined in any order. The stir time employed can range from 0.5 to 48 hours, preferably from 1 to 36 hours, and more preferably from 2 to 24 hours.

Examples of techniques that can be employed to characterize the compositions formed by the process described above include, but are not limited to, analytical gas chromatography, nuclear magnetic resonance, thermogravimetric analysis (TGA), inductively coupled plasma mass spectrometry, differential scanning calorimetry (DSC), volatility and viscosity measurements.

This disclosure provides lubricating oils useful as engine oils and in other applications characterized by excellent solvency and dispersancy characteristics. The lubricating oils are based on high quality basestocks including a major portion of a hydrocarbon base fluid such as a PAO or GTL with a secondary cobasestock component which is an aryl ether as described herein. The lubricating oil basestock can be any oil boiling in the lube oil boiling range, typically between 100 to 450° C. In the present specification and claims, the terms base oil(s) and basestock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

Lubricating Oil Basestocks

A wide range of lubricating oils is known in the art. Lubricating oils that are useful in the present disclosure are both natural oils and synthetic oils. Natural and synthetic oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I basestocks generally have a viscosity index of between 80 to 120 and contain greater than 0.03% sulfur and less than 90% saturates. Group II basestocks generally have a viscosity index of between 80 to 120, and contain less than or equal to 0.03% sulfur and greater than or equal to 90% saturates. Group III stock generally has a viscosity index greater than 120 and contains less than or equal to 0.03% sulfur and greater than 90% saturates. Group IV includes polyalphaolefins (PAO). Group V basestocks include basestocks not included in Groups I-IV. The table below summarizes properties of each of these five groups.

| | Base Oil Properties | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | Includes polyalphaolefins (PAO) products | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked basestocks, as well as synthetic oils such as polyalphaolefins, alkyl aromatics and synthetic esters, i.e. Group IV and Group V oils are also well known basestock oils.

Synthetic oils include hydrocarbon oil such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil basestocks, the Group IV API basestocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO basestocks have viscosity indices preferably greater than 130, more preferably greater than 135, still more preferably greater than 140.

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional basestocks and/or base oils include one or a mixture of basestock(s) and/or base oil(s) derived from: (1) one or more Gas-to-Liquids (GTL) materials, as well as (2) hydrodewaxed, or hydroisomerized/cat (and/or solvent) dewaxed basestock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of 20 or greater, preferably 30 or greater and mixtures of such basestocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL basestocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL basestock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL basestock(s) and/or base oil(s) derived from GTL materials, especially, hydrodewaxed or hydroisomerized/followed by cat and/or solvent dewaxed wax or waxy feed, preferably F-T material derived basestock(s) and/or base oil(s), are characterized typically as having kinematic viscosities at 100° C. of from 2 mm$^2$/s to 50 mm$^2$/s (ASTM D445). They are further characterized typically as having pour points of −5° C. to −40° C. or lower (ASTM D97). They are also characterized typically as having viscosity indices of 80 to 140 or greater (ASTM D2270).

In addition, the GTL basestock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL basestock(s) and/or base oil(s) typically have very low sulfur and nitrogen content, generally containing less than 10 ppm, and more typically less than 5 ppm of each of these elements. The sulfur and nitrogen content of GTL basestock(s) and/or base oil(s) obtained from F-T material, especially F-T wax, is essentially nil. In addition, the absence of phosphorous and aromatics make this materially especially suitable for the formulation of low SAP products.

The term GTL basestock and/or base oil and/or wax isomerate basestock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL basestock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL basestock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL basestock(s) and/or base oil(s) and hydrodewaxed, or hydroisomerized/cat (and/or solvent) dewaxed basestock(s) and/or base oil(s) typically have very low sulfur and nitrogen content, generally containing less than 10 ppm, and more typically less than 5 ppm of each of these elements. The sulfur and nitrogen content of GTL basestock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The basestock component of the present lubricating oils will typically be from 1 to 99 weight percent of the total composition (all proportions and percentages set out in this specification are by weight unless the contrary is stated) and more usually in the range of 10 to 99 weight percent.

Cobasestock Components

Aryl ether-containing cobasestock components useful in this disclosure include, for example, fluids containing one or more compounds represented by formula (1):

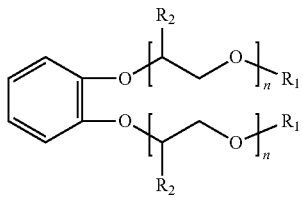

(1)

or by formula (2):

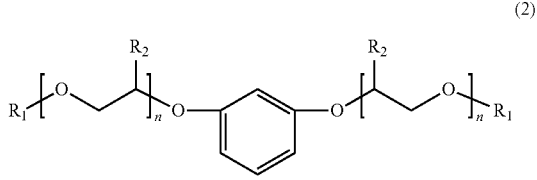

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8. The aryl ether compounds of this disclosure are organic molecules containing hydrocarbon and ether segments with precise structure (i.e., not oligomers or polymers).

The aryl ether-containing cobasestocks of this disclosure include mixtures. Illustrative mixtures include, for example, two or more compounds represented by formula (1); two or more compounds represented by formula (2); and two or more compounds represented by formula (1) and formula (2).

The aryl ether-containing cobasestocks of this disclosure have a viscosity ($Kv_{100}$) from 1 to 30 at 100° C., preferably from 1.25 to 10 at 100° C., and more preferably from 1.5 to 5 at 100° C. The aryl ether-containing cobasestocks have a viscosity ($Kv_{40}$) from 1 to 50 at 40° C., preferably from 2 to 40 at 40° C., and more preferably from 2.5 to 25 at 40° C. The aryl ether-containing cobasestocks have a viscosity index (VI) from 20 to 200, preferably from 25 to 175, and more preferably from 30 to 150. As used herein, viscosity ($Kv_{100}$) is determined by ASTM D 445-01, viscosity ($Kv_{40}$) is determined by ASTM D 445-01, and viscosity index (VI) is determined by ASTM D 2270-93 (1998).

The aryl ether-containing cobasestocks of this disclosure have a Noack volatility of no greater than 50 percent, preferably no greater than 40 percent, and more preferably no greater than 30 percent. As used herein, Noack volatility is determined by ASTM D-5800. In particular, the aryl ether-containing cobasestocks of this disclosure can function in engines without volatilization at specific temperatures (e.g., 247-249° C., Noack conditions).

Illustrative $R_1$ substituents include, for example, linear or branched alkyl groups having from 1 to 20 carbon atoms, preferably linear or branched alkyl groups having from 1 to 10 carbon atoms, and more preferably linear or branched alkyl groups having from 1 to 8 carbon atoms. Illustrative $R_1$ substituents include, for example, methyl, ethyl, propyl, butyl, pentyl, hexyl, heptyl, octyl, and the like. Illustrative $R_2$ substituents include, for example, hydrogen and alkyl groups having from 1 to 4 carbon atoms (e.g., methyl, ethyl, propyl, butyl, and the like). Values of n can range from 0 to 8, preferably from 0 to 6, and more preferably from 0 to 4.

Illustrative aryl ether-containing cobasestock components useful in the present disclosure are described herein.

Methods for the production of the aryl ether-containing cobasestock components suitable for use in the present disclosure are described herein.

The aryl ether-containing cobasestock component is preferably present in an amount sufficient for providing solubility and dispersancy of polar additives and/or sludge in the lubricating oil. The aryl ether-containing cobasestock component is present in the lubricating oils of this disclosure in an amount from 1 to 99 weight percent, preferably from 5 to 95 weight percent, and more preferably from 10 to 90 weight percent.

Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are between 10,000 to 1,000,000, more typically 20,000 to 500,000, and even more typically between 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

Antioxidants

Typical antioxidant include phenolic antioxidants, aminic antioxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such bi-phenol compounds linked by alkylene bridges sulfuric bridges or oxygen bridges. Alkyl phenols include mono- and poly-alkyl or alkenyl phenols, the alkyl or alkenyl group containing from 3-100 carbons, preferably 4 to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

Generally, therefore, the phenolic anti-oxidant may be represented by the general formula:

$(R)_x$—Ar—$(OH)_y$ where Ar is selected from the group consisting of:

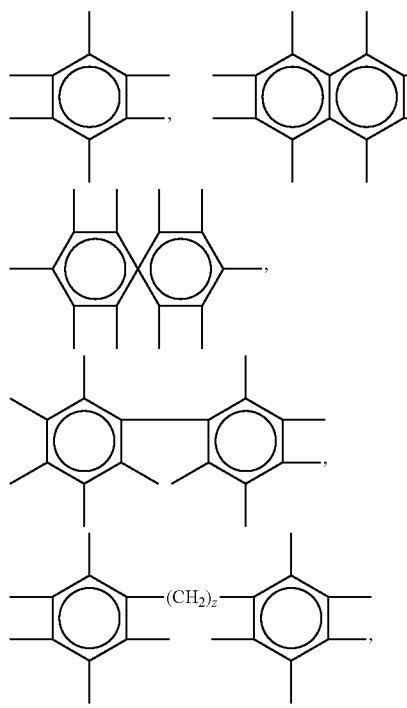

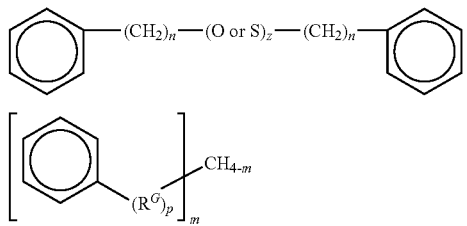

wherein R is a $C_3$-$C_{100}$ alkyl or alkenyl group, a sulfur substituted alkyl or alkenyl group, preferably a $C_4$-$C_{50}$ alkyl or alkenyl group or sulfur substituted alkyl or alkenyl group, more preferably $C_3$-$C_{100}$ alkyl or sulfur substituted alkyl group, most preferably a $C_4$-$C_{50}$ alkyl group, $R^G$ is a $C_1$-$C_{100}$ alkylene or sulfur substituted alkylene group, preferably a $C_2$-$C_{50}$ alkylene or sulfur substituted alkylene group, more preferably a $C_2$-$C_2$ alkylene or sulfur substituted alkylene group, y is at least 1 to up to the available valences of Ar, x ranges from 0 to up to the available valances of Ar-y, z ranges from 1 to 10, n ranges from 0 to 20, and m is 0 to 4 and p is 0 or 1, preferably y ranges from 1 to 3, x ranges from 0 to 3, z ranges from 1 to 4 and n ranges from 0 to 5, and p is 0.

Preferred phenolic antioxidant compounds are the hindered phenolics and phenolic esters which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_1$+ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4 alkoxy phenol; and

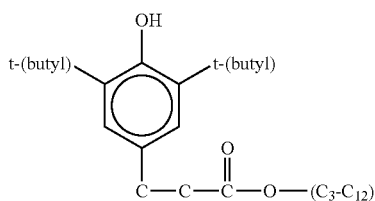

Phenolic type antioxidants are well known in the lubricating industry and commercial examples such as Ethanox® 4710, Irganox® 1076, Irganox® L1035, Irganox® 1010, Irganox® L109, Irganox® L118, Irganox® L135 and the like are familiar to those skilled in the art. The above is presented only by way of exemplification, not limitation on the type of phenolic antioxidants which can be used.

The phenolic antioxidant can be employed in an amount in the range of 0.1 to 3 wt %, preferably 1 to 3 wt %, more preferably 1.5 to 3 wt % on an active ingredient basis.

Aromatic amine antioxidants include phenyl-α-naphthyl amine which is described by the following molecular structure:

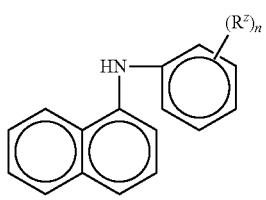

wherein $R^z$ is hydrogen or a $C_1$ to $C_{14}$ linear or $C_3$ to $C_{14}$ branched alkyl group, preferably $C_1$ to $C_{10}$ linear or $C_3$ to $C_{10}$ branched alkyl group, more preferably linear or branched $C_6$ to $C_8$ and n is an integer ranging from 1 to 5 preferably 1. A particular example is Irganox L06.

Other aromatic amine anti-oxidants include other alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^H$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to 20 carbon atoms, and preferably contains from 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least 6 carbon atoms. Examples of aliphatic groups include hexyl, heptyl, octyl, nonyl, and decyl. Generally, the aliphatic groups will not contain more than 14 carbon atoms. The general types of such other additional amine antioxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of antioxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithiophosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and or Cu(II) salts derived from alkenyl succinic acids or anhydrides are known to be particularly useful.

Such antioxidants may be used individually or as mixtures of one or more types of antioxidants, the total amount employed being an amount of 0.50 to 5 wt %, preferably 0.75 to 3 wt % (on an as-received basis).

Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So-called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenyl-succinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from 1:1 to 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from 0.1 to 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and diamino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N—(Z—NH—)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from 500 to 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of 0.1 to 20 wt %, preferably 0.1 to 8 wt %, more preferably 1 to 6 wt % (on an as-received basis) based on the weight of the total lubricant.

Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of 0.0 to 0.5 wt %, preferably 0 to 0.3 wt %, more preferably 0.001 to 0.1 wt % on an as-received basis.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of 0.01 to 5 wt %, preferably 0.01 to 1.5 wt %, more preferably 0.01 to 0.2 wt %, still more preferably 0.01 to 0.1 wt % (on an as-received basis) based on the total weight of the lubricating oil composition.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of 0.01 to 3 wt %, preferably 0.01 to 2 wt % on an as-received basis.

Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to 0.5 wt %, more preferably 0.001 to 0.2 wt %, still more preferably 0.0001 to 0.15 wt % (on an as-received basis) based on the total weight of the lubricating oil composition.

Inhibitors and Antirust Additives

Antirust additives (or corrosion inhibitors) are additives that protect lubricated metal surfaces against chemical attack by water or other contaminants. One type of antirust additive is a polar compound that wets the metal surface preferentially, protecting it with a film of oil. Another type of anti-rust additive absorbs water by incorporating it in a water-in-oil emulsion so that only the oil touches the surface. Yet another type of anti-rust additive chemically adheres to the metal to produce a non-reactive surface. Examples of suitable additives include zinc dithiophosphates, metal phenolates, basic metal sulfonates, fatty acids and amines. Such additives may be used in an amount of 0.01 to 5 wt %, preferably 0.01 to 1.5 wt % on an as-received basis.

In addition to the ZDDP antiwear additives which are essential components of the present disclosure, other antiwear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 cm$^{-1}$ and an amide carbonyl band at 1620 cm$^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Synthesis of 1,2-bis(2-(2-hexyloxy)ethoxy)ethoxy) benzene

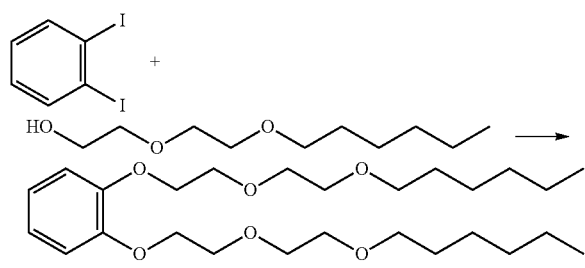

Copper (I) iodide (FW 190.45, 1.80 grams, 9.45 mmol), 1,10-phenathraoline (FW 180.23, 3.30 grams, 18.30 mmol), cesium carbonate (FW 325.82, 38.00 grams, 116.60 mmol), 1,2-diiodobenzene (FW 329.90, 15.00 grams, 45.50 mmol), di(ethylene glycol) hexyl ether (FW 190.28, 26.00 grams, 136.60 mmol) and 100 milliliters of dry xylene were charged in a 500 ml round bottom flask. The reaction mixture was heated with stirring at 140° C. for 72 hours under nitrogen. The resulting suspension was cooled to room temperature and filtered through celite and alumina. The filtrate was concentrated at high vacuum. The residue was purified by flask chromatography on silica gel with 1:1 hexane and ethyl acetate. The final dark yellow product was yielded 17.00 grams (85%). The product IR, and NMR analysis shows the formation of aryl ether product. IR: neat (cm$^{-1}$): 3064, 2929, 2829, 1594, 1501, 1455, 1378, 1353, 1328, 1256, 1221, 1123, 1056, 931, 743. $^1$H NMR (CDCl$_3$): δ 6.75 (m, 4H, Ph), 4.02 (t, 4H, —OCH$_2$—), 3.71 (m, 4H, —CH$_2$O—) 3.56 (m, 4H, —OCH2), 3.44 (m, 4H, —CH$_2$O—,), 3.30 (t, 4H, —OCH$_2$—), 1.43-1.13 (m 16H, —CH$_2$—), 0.73 (t, 6H, —CH$_3$). $^{13}$CNMR (CDCl$_3$): 149.2, 121.8, 115.1, 71.5, 70.9, 70.2, 69.8, 69.0, 31.7, 29.7, 25.8, 22.7, 14.0. GCMS spectrum of mono di(ethylene glycol) hexyl-aryl ether showed m/e at 266.1928. The exact mass for C$_{16}$H$_{26}$O$_3$ would be 266.19. Differential scanning calorimetry (DSC) of the aryl ether of this Example 1 showed no crystallization peak with single low temperature Tg of –82.5° C. suggesting the fluid would have excellent low temperature properties.

Example 2

Synthesis of (2-(2-hexyloxy)ethoxy)ethoxy) benzene

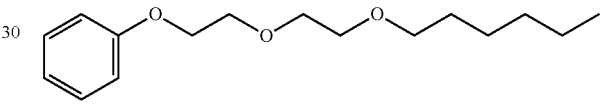

Copper (I) iodide (FW 190.45, 1.91 grams, 10.03 mmol), 1,10-phenathraoline (FW 180.23, 3.55 grams, 19.70 mmol), cesium carbonate (FW 325.82, 48.00 grams, 147.32 mmol), iodobenzene (FW 204.01, 20.00 grams, 98.00 mmol), di(ethylene glycol) hexyl ether (FW 190.28, 28.00 grams, 147.15 mmol) and 75 milliliters of dry xylene were charged in a 350 milliliter round bottom flask. The reaction mixture was heated with stirring at 120° C. for 24 hours under nitrogen. The resulting suspension was cooled to room temperature and filtered through celite and alumina. The filtrate was concentrated at high vacuum. The residue was purified by flask chromatography on silica gel with 1:1 hexane and ethyl acetate. The final light yellow product was yielded 20.00 grams (77%). The product IR, GC/MS and $^1$H NMR analysis shows the formation of aryl ether product. IR: neat (cm$^{-1}$): 2930, 2860, 1600, 1588, 1497, 1455, 1353, 1300, 1247, 1173, 1116, 10821062, 997, 926, 883, 795, 753, 691. $^1$H NMR (CDCl$_3$): δ7.27-6.92 (m 5H, Ph), 4.13 (t, 2H, —OCH$_2$-), 3.87 (t, 2H, —CH$_2$O) 3.70-3.59 (m, 4H, —OCH$_2$—CH$_2$O—), 3.46 (t, 2H), 1.57-1.29 (m, 8H, —CH$_2$—), 0.88 (t, 3H, —CH$_3$).

Example 3

1,2-Bis(octyloxy)benzene fluid was obtained from Sigma-Aldrich (CAS 4956-41-6). Formula: C$_6$H$_4$(O(CH$_2$)$_7$CH$_3$)$_2$, molecular weight: 334.54.

Example 4

Lubricant Properties of Basestocks

The kinematic viscosity (Kv) of the liquid product was measured using ASTM standard D-445 and reported at temperatures of 100° C. (Kv at 100° C.) or 40° C. (Kv at 40° C.). The viscosity index (VI) was measured according to ASTM standard D-2270 using the measured kinematic viscosities for each product. Thermogravimetric analysis (TGA) was measured according to standard procedure. The lube properties of the products of Example 1-3 were evaluated and the data are shown in Table 1 below along with PAO4 and AN5. TGA Noack can be used as Noack surrogate and for the fluid of the Example 1, it was found to be 8.3 which is lower than TGA Noack of 13.45 for PAO4.

The fluids were evaluated as synthetic basestocks and found to have good lubricant properties.

TABLE 1

| Basestock# | Kinematic Viscosity at 100° C. ($Kv_{100}$) | Kinematic Viscosity at 40° C. ($Kv_{40}$) | Viscosity Index (VI) | TGA (50% wt. loss) |
|---|---|---|---|---|
| Example 1 | 3.14 | 13.28 | 94 | 289.5 |
| Example 2 | 1.62 | 4.97 | — | 119.1 |
| Example 3 | 2.14 | 7.99 | 51 | 232 |
| PAO4 | 4.1 | 19 | 126 | 259 |
| AN5 | 4.7 | 29 | 74 | |

The fluid of the Example 1 has lower viscosity than PAO4 ($Kv_{100}$ 3.14 vs. 4.1) but has higher stability (289.5° C. 50% wt. loss vs. 259° C.) than PAO4. Similarly, it has lower viscosity than AN5 ($Kv_{100}$ 3.14 vs. 4.7) but has higher VI (94 vs. 74) than AN5.

TGA can be used for measuring the volatility of synthetic basestocks. The TGA based 50% wt. loss of fluids of this disclosure (Examples 1-3) as well as hydrocarbon fluids like PAO2, PAO4 is shown in the FIG. 1. FIG. 1 graphically depicts TGA (50% wt. loss) of the aryl ether fluids of Examples 1-3 and PAOs of various viscosities. The volatility data clearly show that oxygen containing aryl ether fluids have lower volatility than PAO type hydrocarbon fluids.

By changing the alcohol or glycol ether portion, molecules with varying polarity can be synthesized. The molecules of this disclosure can be used as low viscosity basestock or as co-basestock along with mPAO, PAO, Group I-III+, GTL. Besides basestocks, the molecules of this disclosure can also be used as a non-phthalate, non-ester, but ether based PVC plasticizers.

Example 5

Synthesis of 1,2-bis(2-(2-butyloxy)ethoxy)ethoxy) benzene

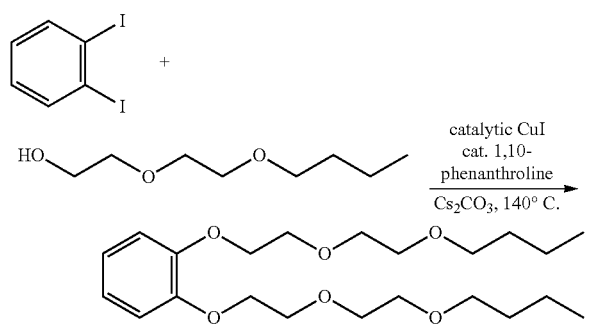

Copper (I) iodide (FW 190.45, 1.80 grams, 9.50 mmol), 1,10-phenanthroline ((FW 180.23, 1.71 grams, 9.50 mmol), cesium carbonate ((FW 325.82, 38.00 grams, 116.60 mmol), 1,2-diiodobenzene (FW 329.90, 15.00 grams, 45.50 mmol), di(ethylene glycol) butyl ether (FW 162.23, 22.15 grams, 136.50 mmol) and 100 milliliters of dry xylene were charged in a 500 milliliter round bottom flask. The reaction mixture was heated with stirring at reflux temperature for 40 hours under nitrogen. The resulting suspension was cooled to room temperature and filtered through celite and alumina. The filtrate was concentrated at high vacuum. The residue was purified by flask chromatography on silica gel with 1:1 hexane and ethyl acetate. The final dark yellow product was yielded 13.50 grams (75%). The product $^1$H NMR analysis shows the formation of aryl ether product. $^1$H NMR (CDCl$_3$): δ 6.89 (m, 4H, Ph), 4.17 (t, 4H, —OCH$_2$—), 3.87 (m, 4H, —CH$_2$O—) 3.72 (m, 4H, —OCH$_2$), 3.59 (m, 4H, —CH$_2$O—,), 3.46 (t, 4H, —OCH$_2$—), 1.43-1.13 (m 4H, —CH$_2$—), 0.91 (t, 6H, —CH$_3$).

Example 6

Synthesis of 1,2-bis(2-butoxyethoxy)benzene Via Reaction of 1,2-diiodobenzene and Ethylene Glycol Butyl Ether

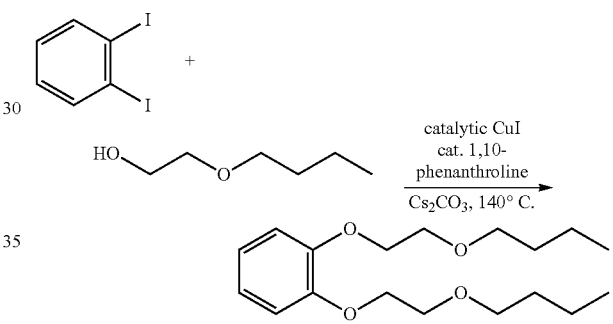

Copper (I) iodide (FW 190.45, 1.20 grams, 6.30 mmol), 1,10-phenanthroline ((FW 180.23, 2.30 grams, 12.80 mmol), cesium carbonate (FW 328.5, 27.30 grams, 83.10 mmol), 1,2-diiodobenzene (FW 329.90, 11.00 grams, 33.34 mmol), ethylene glycol butyl ether (FW 118.11, 11.82 grams, 100.07 mmol) and 100 milliliters of dry xylene were charged in a 350 milliliter round bottom flask. The reaction mixture was heated with stirring at 140° C. for 72 hours under nitrogen. The resulting suspension was cooled to room temperature and filtered through celite and alumina. The filtrate was concentrated at high vacuum. The residue was purified by filter through silica gel. The final dark yellow product was yielded 8.96 grams (88%). The product $^1$H NMR analysis shows the formation of aryl ether product. $^1$H NMR (CDCl$_3$): δ 6.92 (m, 4H, Ph), 4.15 (t, 4H, —OCH$_2$—), 3.78 (m, 4H, —CH$_2$O—) 3.53 (m, 4H, —OCH$_2$), 1.58 (m, 4H, —CH$_2$—), 1.39 (m, 4H, —CH$_2$—) 0.92 (t, 6H, —CH$_3$).

Example 7

Lubricant Properties and Thermal Stability (Surrogate Noack) of Basestocks

The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. TGA can be used for measuring the thermal stability (indicator of volatility) of synthetic basestocks. The lube properties and TGA based 50% wt. loss of the products of Example 5-6 were evaluated and the data are reported in Table 2 below. TGA Noack can be used as Noack surrogate and for the fluid of the Example 5, which was found to be 13.9.

TABLE 2

| Basestock # | Kinematic Viscosity at 100° C. ($Kv_{100}$) | Kinematic Viscosity at 40° C. ($Kv_{40}$) | Viscosity Index (VI) | TGA (50% wt. loss) |
|---|---|---|---|---|
| Example 5 | 2.53 | 10.10 | 65 | 240.1 |
| Example 6 | 1.88 | — | — | 200.2 |

Example 8

Synthesis of 1,2-bis(octyloxy)benzene

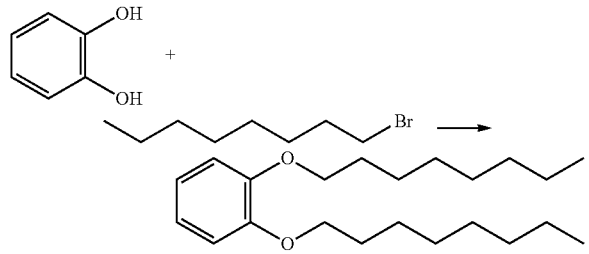

Aryl ethers can be synthesized by the reaction of diiodobenzene with alkyl alcohol (Oxo alcohol) or glycol ethers. The aryl ethers can also be synthesized by alternate etherification coupling reaction. For example, aryl ether molecules can be synthesized by the reaction of catechol with alkyl halides as described below.

Figure 2:
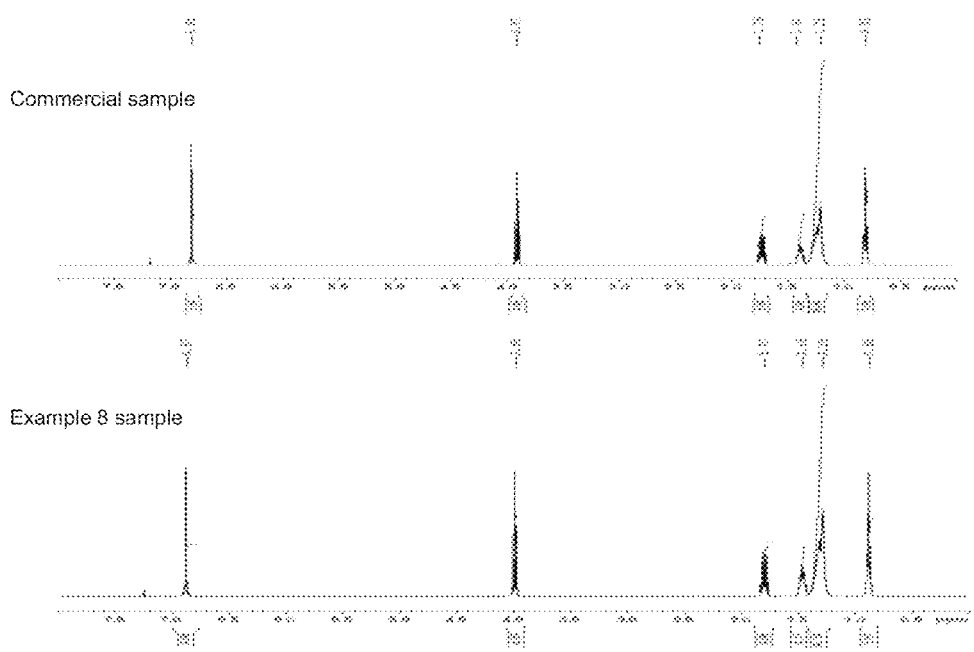
FIG. 2 depicts $^1$H NMR spectra of 1,2-bis(octyloxy) benzene (commercial sample and sample of Example 8.

1,2-Dihydroxybenzene (FW 110.11, 5.00 grams, 45.40 mmol), potassium carbonate (FW 138.21, 13.80 grams, 99.90 mmol), benzyl tributylammonium bromide (FW 356.38, 2.43 grams, 6.80 mmol) and 75 milliliters of acetone were charged in a 350 milliliter two necked round bottom flask under $N_2$ atmosphere. 1-Bromooctane (FW 193.12, 21.92 grams, 113.50 mmol) was slowly added at room temperature. After addition, the reaction mixture was stirred for 26 hours at reflux temperature. The reaction was stopped by adding 100 milliliters of water. The acetone was evaporated and the product extracted with (2×75 milliliters) hexane. The organic extract was washed with (2×50 milliliters) 2N saturated NaOH solution and water (1×75 milliliters) until, the aqueous layer pH ~7. The product was dried and filtered. The low boiling (hexane) component was removed by rotavapory and high boiling component (1-bromooctane) by air bath oven at 200° C. under high vacuum for 2 hours. The final product was determined by $^1$H NMR. Yields: 11.50 grams (76%). $^1$H NMR (CDCl$_3$): δ 6.81 (m, 4H, Ph), 3.98 (t, 4H, —OCH$_2$—), 1.76 (m, 4H, —CH$_2$—) 1.42 (m, 4H, —CH$_2$—), 1.21 (m, 16H, —CH$_2$—) 0.81 (t, 6H, —CH$_3$). FIG. 2 shows $^1$H NMR spectra of 1,2-bis (octyloxy) benzene (i.e., a commercial sample and a sample of this Example 8).

The fluid of Example 8 has kinematic viscosity of 2.53 cSt and TGA shows 50% wt. loss of 240.1° C. TGA can be considered as surrogate to Noack test that is carried out at 247-249° C. Thus, the fluid of the Example 5 may evaporate in the engine. The fluid of this Example 1 (see Table 3 below) has the kinematic viscosity of 3.14 cSt, and TGA shows 50% wt. loss of 289.5° C. This fluid is substantially more stable.

Example 9

"Single-Molecule" Aryl Ether Basestock Blends: Blend of Fluids of Example 1 and Example 5

The fluids of Example 1 and Example 5 were combined in 50:50 wt. % ratio and evaluated for its lube and volatility properties. The results are shown in Table 3 below.

Example 10

Lubricant Properties of Basestocks

Figure 3:
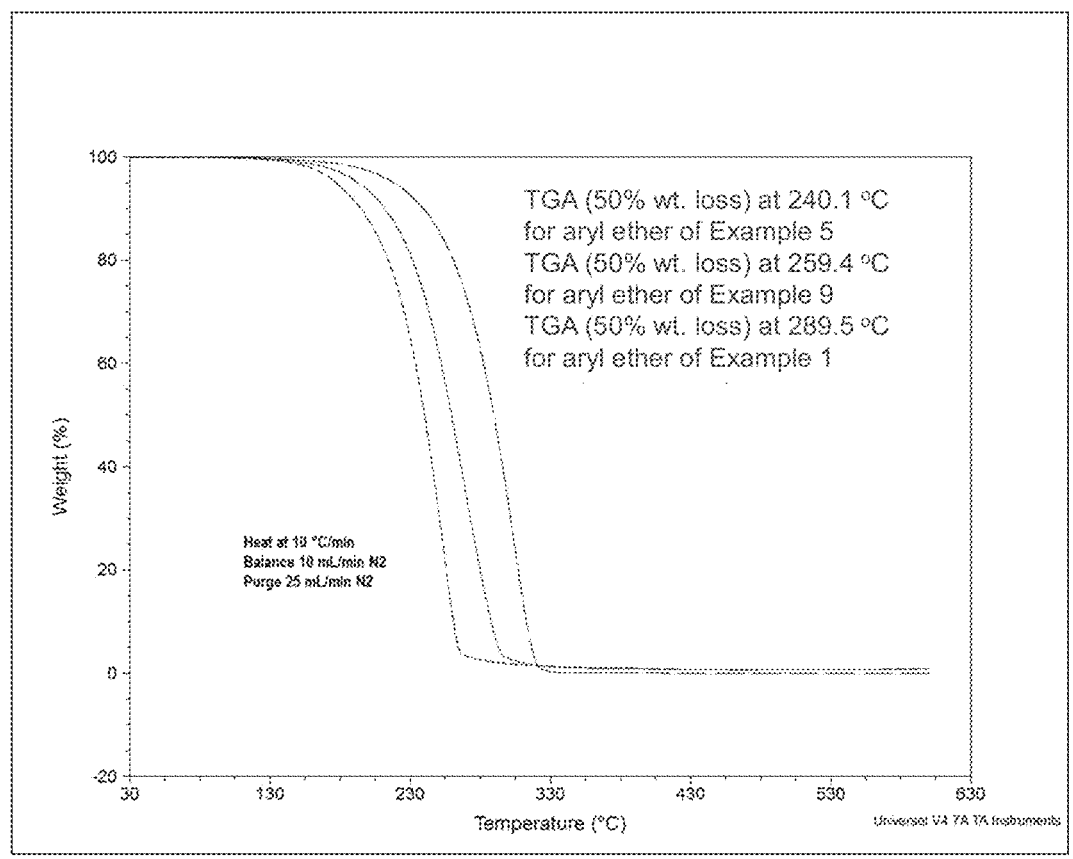
FIG. 3 shows the TGA scans of the fluids of Examples 1, 5 and 10.

The kinematic viscosity (Kv) of the liquid products was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. TGA can be used for measuring the thermal stability (indicator of volatility) of synthetic basestocks. The lube properties and TGA based 50% wt. loss of the products of Examples 8, 1 and 9 were evaluated and the data are reported in Table 3 below. Table 3 shows lubricant properties and thermal stability of fluids of Examples 8, 1 and 9 (blend of fluids of Examples 1 and 8). The TGA scans of the fluids of Examples 8, 1 and 9 are shown in FIG. 3.

TABLE 3

| Basestock # | Kinematic Viscosity at 100° C. ($Kv_{100}$) | Kinematic Viscosity at 40° C. ($Kv_{40}$) | Viscosity Index (VI) | TGA (50% wt. loss) |
|---|---|---|---|---|
| Example 8 | 2.53 | 10.10 | 65 | 240.1 |
| Example 1 | 3.14 | 13.28 | 94 | 289.5 |
| Example 9 | 2.79 | 11.35 | 80 | 259.4 |

TGA shows for the fluid of Example 9 (blend) a 50% wt. loss of 259.4° C. TGA can be considered as surrogate Noack test that is carried out at 247-249° C. Thus, the 50% wt. loss temperature of fluid of Example 10 (blend) is higher than temperature of the Noack test.

These molecules can be used as low viscosity basestock or they can be used as co-basestock along with mPAO, PAO, Group I-III+, and GTL basestocks. In addition to basestocks, these molecules can also be used as a non-phthalate, non-ester, but ether based PVC plasticizers.

Example 11

Synthesis of 1,3-bis(2-(2-(2-ethoxyethoxy)ethoxy)ethoxy)benzene

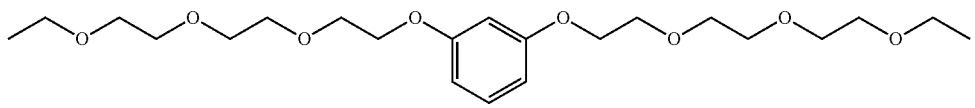 [SMILES: CCOCCOCCOCCOc1cccc(OCCOCCOCCOCC)c1]

Copper (I) iodide (FW 190.45, 0.90 grams, 4.72 mmol), 1,10-phenanthroline (FW 180.21, 0.83 grams, 4.62 mmol), cesium carbonate (FW 325.82, 19.00 grams, 58.30 mmol), 1,3-diiodobenzene (FW 329.90, 7.50 grams, 22.7 mmol), tri(ethylene glycol) ethyl ether (FW 178.23, 16.25 grams, 91.17 mmol) and 100 milliliters of dry xylene were charged in a 350 milliliter three necked round bottom flask. The reaction mixture was heated with stirring at reflux temperature for 20 hours under nitrogen. The resulting suspension was cooled to room temperature by adding 50 milliliters of toluene. Then reaction mixture was filtered through celite, alumina and silica gel. The low boiling (xylene and toluene) component was removed by a rotary evaporator and high boiling component tri(ethylene glycol) ethyl ether by air bath oven at 200° C. under high vacuum for 2 hours. The final dark yellow product was yielded 7.00 grams (71%). The product IR and $^{13}$C NMR analysis shows the formation of aryl ether product. IR: neat (cm$^{-1}$): 687, 764, 845, 949, 996, 1113, 1185, 1264, 1289, 1333, 1349, 1374, 1418, 1452, 1492, 1590, 2869, 2972. $^{13}$C NMR (CDCl$_3$): 160.02, 130.03, 107.17, 101.76, 70.81, 70.68, 70.61, 69.79, 69.67, 67.40, 66.53, 15.24.

Example 12

Synthesis of 1,3-bis(2-(2-(2-methoxyethoxy)ethoxy)ethoxy) benzene

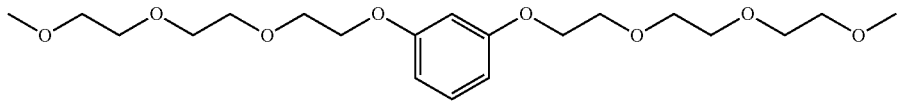

Copper (I) iodide (FW 190.45, 0.90 grams, 4.72 mmol), 1,10-phenanthroline (FW 180.21, 0.83 grams, 4.62 mmol), cesium carbonate (FW 325.82, 19.00 grams, 58.30 mmol), 1,3-diiodobenzene (FW 329.90, 7.50 grams, 22.70 mmol), tri(ethylene glycol) methyl ether (FW 164.20, 14.95 grams, 91.00 mmol) and 100 milliliters of dry xylene were charged in a 350 milliliter three necked round bottom flask. The reaction mixture was heated with stirring at reflux temperature for 20 hours under nitrogen. The resulting suspension was cooled to room temperature by adding 50 milliliters of toluene. Then reaction mixture was filtered through celite, alumina and silica gel. The low boiling (xylene and toluene) component was removed by a rotary evaporator and high boiling component tri(ethylene glycol) methyl ether by air bath oven at 200° C. under high vacuum for 2 hours. The final dark yellow product was yielded 7.5 grams (82%). The product IR and $^{13}$C NMR analysis shows the formation of aryl ether product. IR: neat (cm$^{-1}$): 687, 736, 765, 847, 985, 1125, 1185, 1264, 1288, 1332, 1351, 1418, 1452, 1492, 1590, 2875. $^{13}$C NMR (CDCl$_3$): 159.72, 129.74, 107.13, 101.72, 71.95, 70.76, 70.61, 70.51, 69.71, 67.42, 59.03.

Example 13

Synthesis of 1,3-bis(2-(2-butylethoxy) ethoxy) benzene

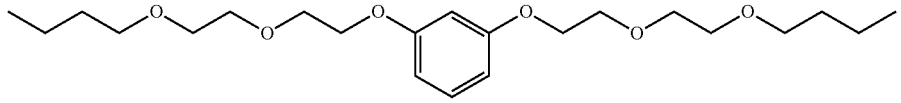 [SMILES: CCCCOCCOCCOc1cccc(OCCOCCOCCCC)c1]

Copper (I) iodide (FW 190.45, 0.90 grams, 4.72 mmol), 1,10-phenanthroline (FW 180.21, 0.83 grams, 4.62 mol), cesium carbonate (FW 325.82, 19.00 grams, 58.30 mmol), 1,3-diiodobenzene (FW 329.90, 7.50 grams, 22.70 mmol), di(ethylene glycol) butyl ether (FW 162.23, 11.06 grams, 68.17 mmol) and 100 milliliters of dry xylene were charged in a 350 milliliter three necked round bottom flask. The reaction mixture was heated with stirring at reflux temperature for 20 hours under nitrogen. The resulting suspension was cooled to room temperature by adding 50 milliliters of toluene. Then reaction mixture was filtered through celite, alumina and silica gel. The low boiling (xylene and toluene) component was removed by a rotary evaporator and high boiling component di(ethylene glycol) butyl ether by air bath oven at 200° C. under high vacuum for 2 hours. The final dark yellow product was yielded 7.80 grams (86%). The product IR and $^{13}$C NMR analysis shows the formation of aryl ether product. IR: neat (cm$^{-1}$): 686, 761, 839, 932, 1059, 1123, 1183, 1263, 1288, 1333, 1353, 1454, 1492, 1591, 2870, 2932, 2957. $^{13}$C NMR (CDCl$_3$): 159.92, 129.64, 106.80, 101.84, 71.58, 70.88, 70.12, 69.71, 67.42, 31.71, 29.62, 25.79, 22.61, 15.0.

Example 14

Synthesis of 1,2-bis(2-(2-(2-methoxyethoxy)ethoxy)ethoxy) benzene

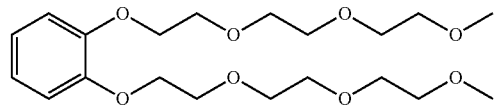 [SMILES: COCCOCCOCCOc1ccccc1OCCOCCOCCOC]

Copper (I) iodide (FW 190.45, 0.90 grams, 4.72 mol), 1,10-phenanthroline (FW 180.21, 0.83 grams, 4.62 mol), cesium carbonate (FW 325.82, 19.00 grams, 8.30 mol), 1,2-diiodobenzene (FW 329.90, 7.50 grams, 22.70 mmol), tri(ethylene glycol) methyl ether (FW 164.29, 11.19 grams, 68.10 mmol) and 100 milliliters dry xylene were charged in a 350 milliliter three necked round bottom flask. The reaction mixture was heated with stirring at reflux temperature for 20 hours under nitrogen. The resulting suspension was cooled to room temperature by adding 50 milliliters of toluene. Then reaction mixture was filtered through celite and alumina. The low boiling (xylene and toluene) component was removed by a rotary evaporator and high boiling component tri(ethylene glycol) methyl ether by air bath oven at 200° C. under high vacuum for 2 hours. The residue was purified by flask chromatography on silica gel. The final dark yellow product was yielded 5.0 grams (54%). The product IR and $^{13}$C NMR analysis shows the formation of aryl ether product. IR: neat (cm$^{-1}$): 746, 850, 931, 1054, 1112, 1200, 1256, 1327, 1351, 1453, 1501, 1592, 2874. $^{13}$C NMR (CDCl$_3$): 149.17, 122.11, 115.04, 71.91, 70.78, 70.66, 70.51, 69.77, 68.88, 58.9.

Example 15

Synthesis of 1,2-bis(2-(2-ethylethoxy) ethoxy) benzene

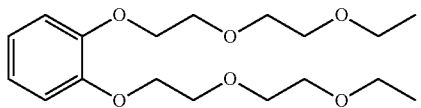 [SMILES: CCOCCOCCOc1ccccc1OCCOCCOCC]

Copper (I) iodide (FW 190.45, 0.90 grams, 4.72 mmol), 1,10-phenanthroline (FW 180.21, 0.83 grams, 4.62 mmol), cesium carbonate (FW 325.82, 19.00 grams, 58.30 mmol), 1,2-diiodobenzene (FW 329.90, 7.50 grams, 22.70 mol), di(ethylene glycol) ethyl ether (FW 134.17, 9.18 grams, 68.40 mol) and 100 milliliters of dry xylene were charged in a 350 milliliter three necked round bottom flask. The reaction mixture was heated with stirring at reflux temperature for 20 hours under nitrogen. The resulting suspension was cooled to room temperature by adding 50 milliliters of toluene. Then reaction mixture was filtered through celite and alumina. The low boiling (xylene and toluene) component was removed by a rotary evaporator and high boiling component di(ethylene glycol) ethyl ether by air bath oven at 200° C. under high vacuum for 2 hours. The residue was purified by flask chromatography on silica gel. The final dark yellow product yielded 7.00 grams (90%). The product IR and $^{13}$C NMR analysis shows the formation of aryl ether product. IR: neat (cm$^{-1}$): 745, 843, 931, 1052, 1116, 1219, 1256, 1325, 1350, 1373, 1453, 1501, 1593, 2869, 2929, 2973. $^{1}$H NMR (CDCl$_3$): δ 6.76 (m, 4H, Ph), 4.02 (t, 4H, —OCH$_2$—), 3.71 (m, 4H, —CH$_2$O—) 3.57 (m, 4H, —OCH$_2$), 3.45 (m, 4H, —OCH$_2$—), 3.37 (t, 4H, —OCH$_2$—), 1.06 (t, 6H, —CH$_3$). $^{13}$C NMR (CDCl$_3$): 149.42, 121.61, 115.04, 70.89, 69.89, 69.76, 68.93, 66.59, 15.14.

Example 16

Lubricant Properties of Basestocks

The kinematic viscosity (Kv) of the liquid products was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The lube properties were evaluated and the data are reported in Table 4 below.

The fluids listed in Table 4 were evaluated as synthetic basestocks and found to have good lubricant properties. These fluids can be used as lubricant basestocks and co-basestocks.

TABLE 4

| Basestock # | Kv$_{100}$ ° C. | Kv$_{40}$ ° C. | Viscosity Index | TGA Noack |
|---|---|---|---|---|
| Example 11 | 2.85 | 12.62 | 76 | 8.13 |
| Example 12 | 3.81 | 19.36 | 74 | 11.11 |
| Example 13 | 3.44 | 15.64 | 90 | 9.31 |
| Example 14 | 3.12 | 14.00 | 71 | 6.32 |
| Example 15 | 2.13 | 8.03 | 45 | 22.42 |

Example 17

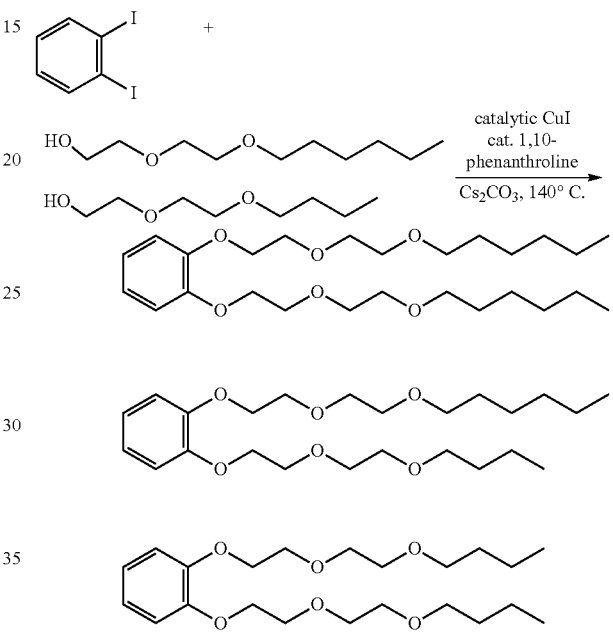

Copper (I) iodide (FW 190.45, 0.827 grams, 4.34 mmol), 1,10-phenathraoline (FW 180.23, 0.764 grams, 4.24 mmol), cesium carbonate (FW 325.82, 17.41 grams, 53.0 mmol), 1,2-diiodobenzene (FW 329.90, 7.0 grams, 21.2 mmol), di(ethylene glycol) hexyl ether (FW 190.28, 5.16 grams, 31.8 mmol), di(ethylene glycol) butyl ether (FW 162.23, 6.1 grams, 31.8 mmol) and 75 milliliters of dry xylene were charged in a 500 milliliter round bottom flask. The reaction mixture was heated with stirring at 140° C. for 40 hours under nitrogen. The resulting suspension was cooled to room temperature and filtered through celite and alumina. The filtrate was concentrated at high vacuum. The residue was purified by flask chromatography on silica gel with 1:1 hexane and ethyl acetate. The final dark yellow product was yielded 8.5 grams (89%). The product NMR analysis shows the formation of aryl ether product. $^{1}$H NMR (CDCl$_3$): δ 6.92 (m, 12H, Ph), 4.17 (t, 12H, —OCH$_2$—), 3.87 (m, 12H, —CH$_2$O—) 3.72 (m, 12H, —OCH$_2$), 3.60 (m, 12H, —CH$_2$O—,), 3.47 (t, 12H, —OCH$_2$—), 1.57-8.18 (m 40H, —CH$_2$—), 0.91 (t, 18H, —CH$_3$). $^{13}$C NMR (CDCl$_3$): 148.97, 121.82, 114.97, 71.56, 71.24, 70.89, 70.15, 69.76, 68.88, 31.72, 29.60, 25.76, 22.63, 19.27, 14.05, 13.90.

The fluids were evaluated as synthetic basestocks and found to have good lubricant properties. For example, the kinematic viscosity (Kv) of the liquid products at temperatures of 100° C. (Kv at 100° C.) was 2.81 cSt and at temperature of 40° C. (Kv at 40° C.) was 11.33 cSt and the viscosity index (VI) was 86. The TGA Noack of the product was 11.3. Thus, the fluids have low viscosity and low volatility.

PCT and EP Clauses:

1. A compound represented by formula (1):

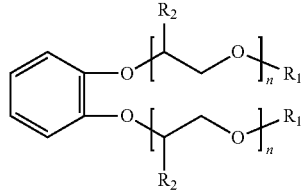
(1)

or a compound represented by formula (2):

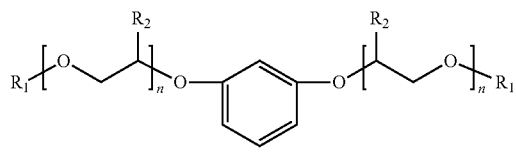
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

2. The compound of clause 1 which has a kinematic viscosity (Kv) at a temperature of 100° C. (Kv at 100° C.), measured according to ASTM standard D-445, from 1 to 30; a kinematic viscosity (Kv) at a temperature of 40° C. (Kv at 40° C.), measured according to ASTM standard D-445, from 1 to 50; a viscosity index (VI), measured according to ASTM standard D-2270, from 20 to 200; and a Noack volatility, measured according to ASTM D-5800, of no greater than 50 percent.

3. The compound of clauses 1 and 2, wherein formula (1) is represented by the formula selected from the group consisting of:

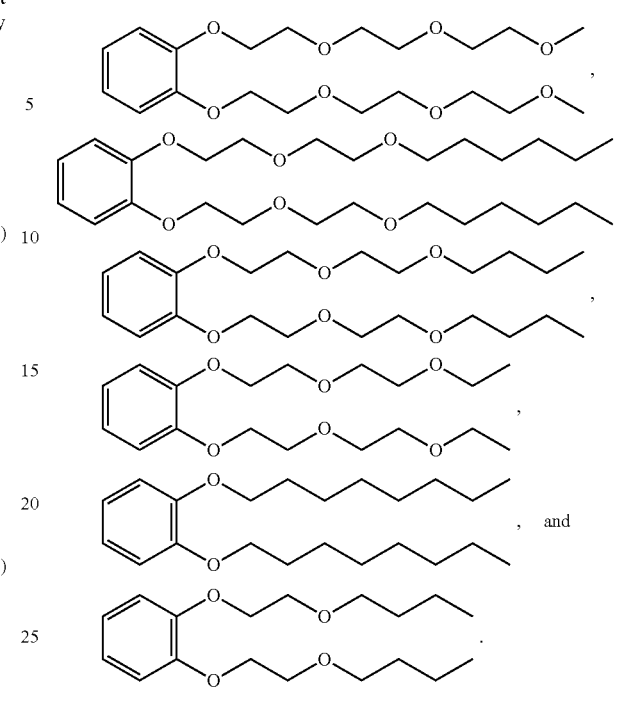
, and

4. The compound of clauses 1 and 2, wherein formula (2) is represented by the formula:

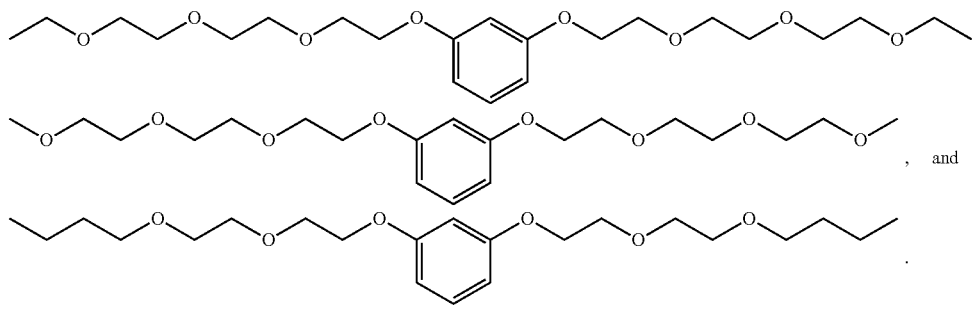
, and

5. A mixture comprising: two or more compounds represented by formula (1) of clauses 1-3; two or more compounds represented by formula (2) of clauses 1, 2 an 4; or two or more compounds represented by formula (1) and formula (2) of clauses 1-4.

6. A process for producing a compound represented by formula (1):

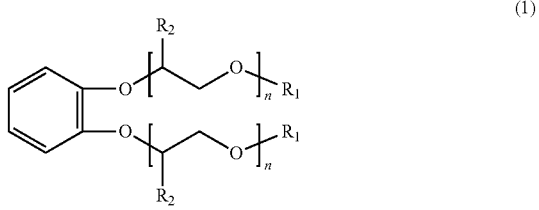
(1)

or a compound represented by formula (2):

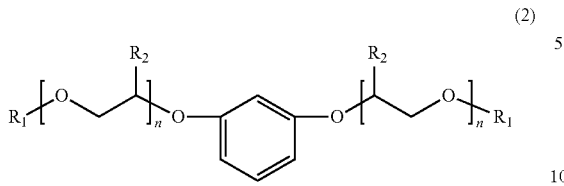
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8; said process comprising reacting an aryl halide with an alcohol, in the presence of a catalyst, under reaction conditions sufficient to produce said compound represented by formula (1) or said compound represented by formula (2).

7. A process for producing a compound represented by formula (1):

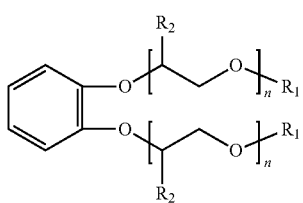
(1)

or a compound represented by formula (2):

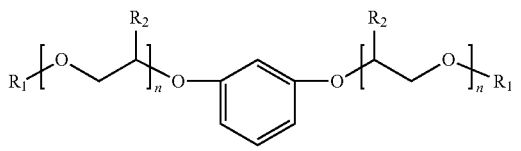
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8; said process comprising reacting an aryl diol with an alkyl halide, in the presence of a catalyst, under reaction conditions sufficient to produce said compound represented by formula (1) or said compound represented by formula (2).

8. A lubricating oil basestock comprising one or more compounds represented by formula (1):

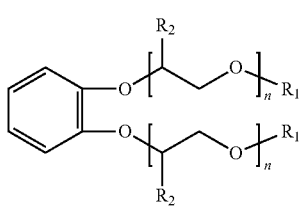
(1)

and/or by formula (2):

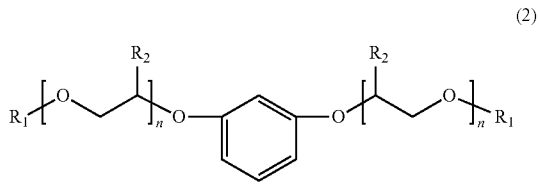
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

9. The lubricating oil basestock of clause 8 which has a kinematic viscosity (Kv) at a temperature of 100° C. (Kv at 100° C.), measured according to ASTM standard D-445, from 1 to 30; a kinematic viscosity (Kv) at a temperature of 40° C. (Kv at 40° C.), measured according to ASTM standard D-445, from 1 to 50; a viscosity index (VI), measured according to ASTM standard D-2270, from 20 to 200; and a Noack volatility, measured according to ASTM D-5800, of no greater than 50 percent.

10. The lubricating oil basestock of clauses 8 and 9 which comprises a mixture of two or more compounds represented by formula (1); two or more compounds represented by formula (2); or two or more compounds represented by formula (1) and formula (2).

11. A lubricating oil comprising a lubricating oil basestock as a major component, and a lubricating oil cobasestock as a minor component; wherein said lubricating oil cobasestock is represented by formula (1):

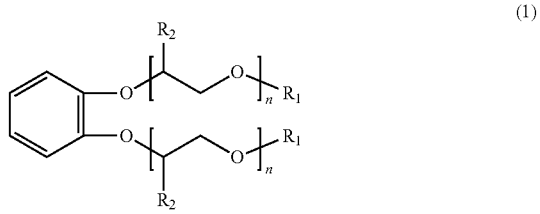
(1)

or by formula (2):

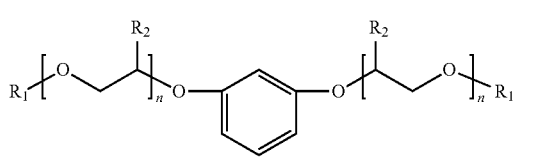
(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

12. The lubricating oil of clause 11 wherein the lubricating oil basestock comprises a Group I, II, III, IV or V base oil stock.

13. The lubricating oil of clauses 11 and 12 wherein the lubricating oil cobasestock of formula (1) is represented by the formula selected from the group consisting of:

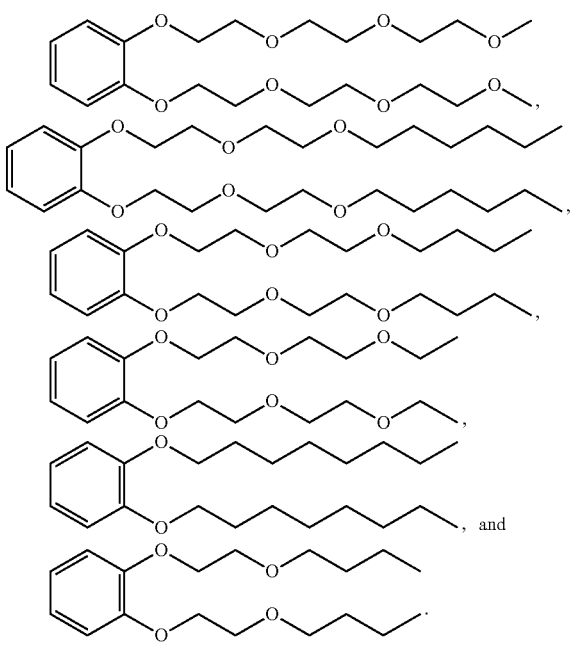

14. The lubricating oil of clauses 11 and 12 wherein the lubricating oil cobasestock of formula (2) is represented by the formula selected from the group consisting of:

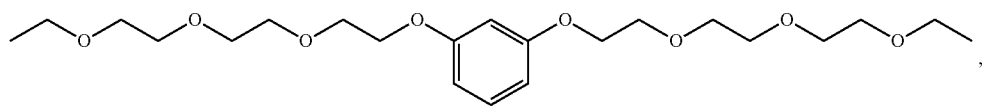

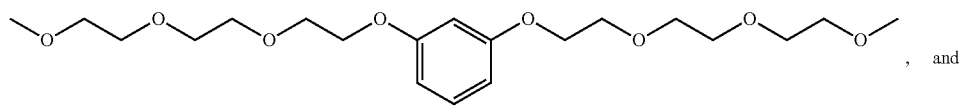, and

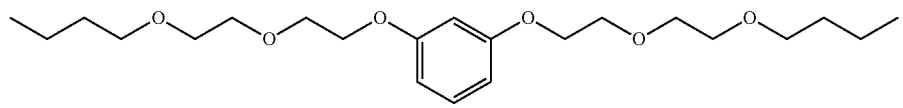.

15. A method for improving one or more of solubility and dispersancy of polar additives or sludge in a lubricating oil by using as the lubricating oil a formulated oil comprising a lubricating oil basestock as a major component, and a lubricating oil cobasestock as a minor component; wherein said lubricating oil cobasestock comprises one or more compounds represented by formula (1):

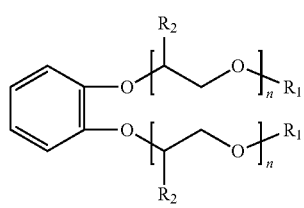

or one or more compounds represented by formula (2):

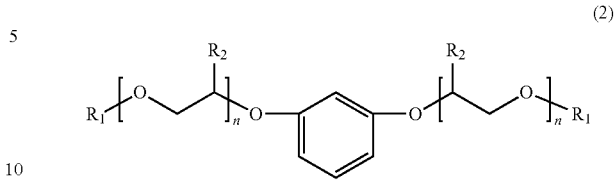

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A lubricating oil basestock comprising one or more compounds represented by formula (1):

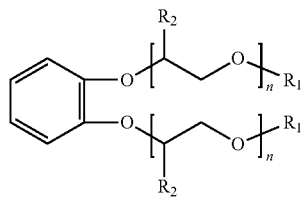

and/or by formula (2):

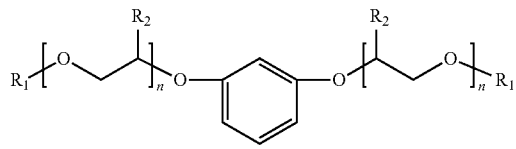

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8; and wherein the lubricating oil basestock has a kinematic viscosity at 100° C., measured according to ASTM standard D-445, of from 1.5 to 3.81 cSt and a Noack volatility of no greater than 30 percent, determined by ASTM D-5800.

2. The lubricating oil basestock of claim 1 which comprises a mixture of two or more compounds represented by formula (1); two or more compounds represented by formula (2); or two or more compounds represented by formula (1) and formula (2).

3. The lubricating oil basestock of claim 1 which has a kinematic viscosity (Kv) at a temperature of 40° C. (Kv at 40° C.), measured according to ASTM standard D-445, from 1 to 50 cSt; and a viscosity index (VI), measured according to ASTM standard D-2270, from 20 to 200.

4. A lubricating oil comprising a lubricating oil basestock as a major component, and a lubricating oil cobasestock as a minor component; wherein said lubricating oil cobasestock is represented by formula (1):

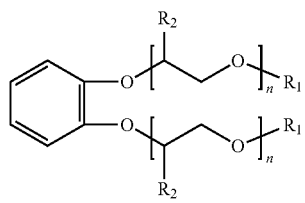

or by formula (2):

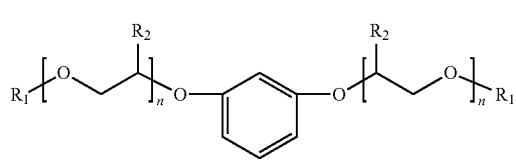

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8; and wherein said lubricating oil cobasestock has a kinematic viscosity at 100° C., measured according to ASTM standard D-445, of from 1.5 to 3.81 cSt and a Noack volatility of no greater than 30 percent, determined by ASTM D-5800.

5. The lubricating oil of claim 4 wherein the lubricating oil basestock comprises a Group I, II, III, IV or V base oil stock.

6. The lubricating oil of claim 4 wherein the lubricating oil basestock comprises a polyalphaolefin (PAO) or gas-to-liquid (GTL) oil basestock.

7. The lubricating oil of claim 4 wherein the lubricating oil basestock is present in an amount from 1 weight percent to 99 weight percent, and the lubricating oil cobasestock is present in an amount from 1 weight percent to 99 weight percent, based on the total weight of the lubricating oil.

8. The lubricating oil of claim 4 wherein, in the lubricating oil cobasestock, $R_1$ is a linear or branched alkyl group having from 1 to 10 carbon atoms; $R_2$ is hydrogen; and n is a value from 0 to 6.

9. The lubricating oil of claim 4 wherein, in the lubricating oil cobasestock, $R_1$ is a linear or branched alkyl group having from 1 to 8 carbon atoms; $R_2$ is hydrogen; and n is a value from 0 to 4.

10. The lubricating oil of claim 4, wherein the lubricating oil cobasestock of formula (1) is represented by the formula selected from the group consisting of:

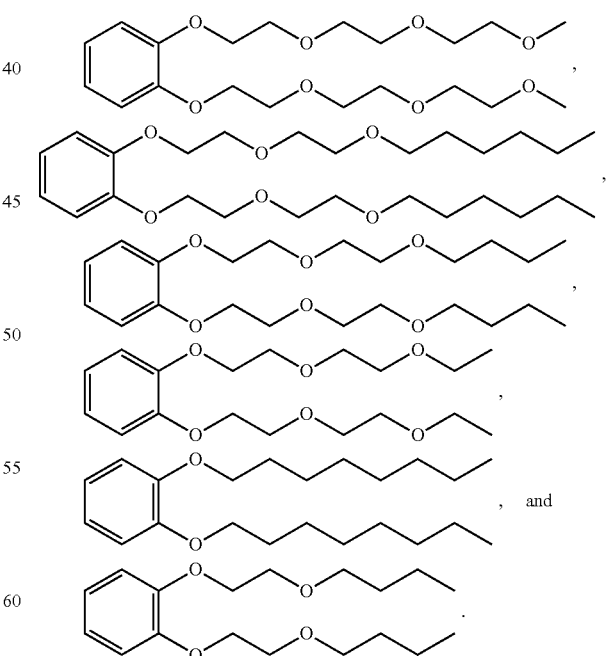

11. The lubricating oil of claim 4, wherein the lubricating oil cobasestock of formula (2) is represented by the formula selected from the group consisting of:

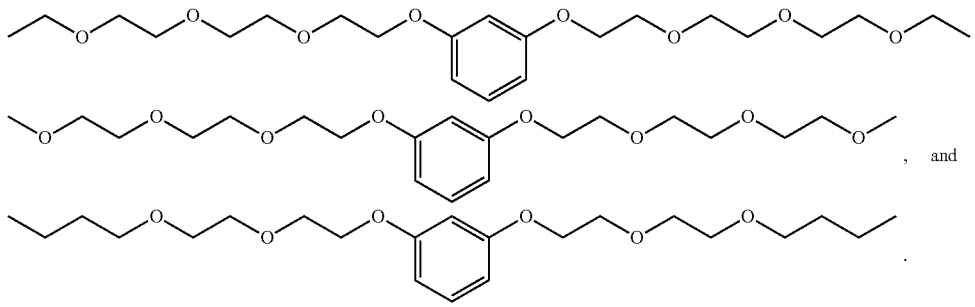
, and

12. The lubricating oil of claim 4, wherein the lubricating oil cobasestock is mixture comprising two or more compounds represented by formula (1); two or more compounds represented by formula (2); or two or more compounds represented by formula (1) and formula (2).

13. The lubricating oil of claim 4 wherein the lubricating oil cobasestock has a kinematic viscosity (Kv) at a temperature of 40° C. (Kv at 40° C.), measured according to ASTM standard D-445, from 1 to 50 cSt; and a viscosity index (VI), measured according to ASTM standard D-2270, from 20 to 200.

14. The lubricating oil of claim 4 further comprising one or more of a viscosity improver, antioxidant, detergent, dispersant, pour point depressant, corrosion inhibitor, metal deactivator, seal compatibility additive, anti-foam agent, inhibitor, and anti-rust additive.

15. A method for improving one or more of solubility and dispersancy of polar additives or sludge in a lubricating oil by using as the lubricating oil a formulated oil comprising a lubricating oil basestock as a major component, and a lubricating oil cobasestock as a minor component; wherein said lubricating oil cobasestock comprises one or more compounds represented by formula (1):

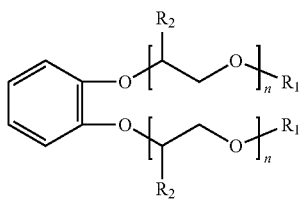

(1)

or one or more compounds represented by formula (2):

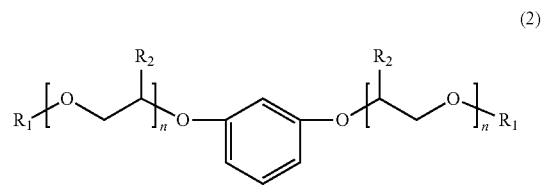

(2)

wherein $R_1$ is the same or different and is a linear or branched alkyl group having from 1 to 20 carbon atoms; $R_2$ is the same or different and is hydrogen or an alkyl group having from 1 to 4 carbon atoms; and n is the same or different and is a value from 0 to 8; and wherein said lubricating oil cobasestock has a kinematic viscosity at 100° C., measured according to ASTM standard D-445, of from 1.5 to 3.81 cSt and a Noack volatility of no greater than 30 percent, determined by ASTM D-5800.

16. The method of claim 15, wherein the lubricating oil cobasestock is mixture comprising two or more compounds represented by formula (1); two or more compounds represented by formula (2); or two or more compounds represented by formula (1) and formula (2).

17. The method of claim 15 wherein the lubricating oil cobasestock has a kinematic viscosity (Kv) at a temperature of 100° C. (Kv at 100° C.), measured according to ASTM standard D-445, from 1.5 to 5 cSt; a kinematic viscosity (Kv) at a temperature of 40° C. (Kv at 40° C.), measured according to ASTM standard D-445, from 1 to 50 cSt; and a viscosity index (VI), measured according to ASTM standard D-2270, from 20 to 200.

\* \* \* \* \*